(12) United States Patent
Eberle et al.

(10) Patent No.: US 10,202,574 B2
(45) Date of Patent: Feb. 12, 2019

(54) INCUBATOR

(71) Applicant: ANDREAS HETTICH GMBH & CO. KG, Tuttlingen (DE)

(72) Inventors: Klaus-Guenter Eberle, Tuttlingen (DE); Natascha Schaldecker, Tuttlingen (DE)

(73) Assignee: ANDREAS HETTICH GMBH & CO. KG, Tuttlingen (DE)

( * ) Notice: Subject to any disclaimer, the term of this patent is extended or adjusted under 35 U.S.C. 154(b) by 27 days.

(21) Appl. No.: 15/127,029

(22) PCT Filed: Mar. 17, 2015

(86) PCT No.: PCT/EP2015/055587
§ 371 (c)(1),
(2) Date: Sep. 19, 2016

(87) PCT Pub. No.: WO2015/140186
PCT Pub. Date: Sep. 24, 2015

(65) Prior Publication Data
US 2017/0121662 A1    May 4, 2017

(30) Foreign Application Priority Data
Mar. 21, 2014  (DE) .................. 10 2014 103 948

(51) Int. Cl.
*G01N 1/00* (2006.01)
*C12M 1/00* (2006.01)
(Continued)

(52) U.S. Cl.
CPC ............ *C12M 41/14* (2013.01); *C12M 23/04* (2013.01); *C12M 23/48* (2013.01)

(58) Field of Classification Search
CPC ..................................................... A47B 88/04
See application file for complete search history.

(56) References Cited

U.S. PATENT DOCUMENTS

| 4,572,427 A | 2/1986 | Selfridge |
| 4,696,902 A | 9/1987 | Bisconte |

(Continued)

FOREIGN PATENT DOCUMENTS

| DE | 19816 962 C1 | 10/1999 |
| DE | 19816962 C1 | 10/1999 |

(Continued)

OTHER PUBLICATIONS

PCT/EP2015/055587 International Search Report and Written Opinion, dated Jun. 29, 2015, 17 Pages.

(Continued)

*Primary Examiner* — Jyoti Nagpaul
(74) *Attorney, Agent, or Firm* — Woodling, Krost and Rust

(57) ABSTRACT

The invention relates to an incubator (10) for creating and maintaining a microclimate with controlled air humidity and temperature conditions. The incubator has a tray opening (12) for inserting trays (16) into an internal space which is bounded by walls (14a, 14b, 14c, 14d), as well as telescopic rails (20) having a first rail part (34) which can be connected to a side wall (14a, 14b) and a further second rail part (35) which can be connected to the tray (16). The invention is characterized in that the telescopic rails (20) are formed as components separately from the internal space of the incubator and from the trays (16), in that supports (22, 28) for the telescopic rails (20) are provided on the side walls (14), and in that the trays (16) can be detached from the telescopic rails (20) and the telescopic rails (20) can be detached from the supports (22, 28).

8 Claims, 5 Drawing Sheets

(51) Int. Cl.
*C12M 1/12* (2006.01)
*C12M 3/00* (2006.01)

(56) References Cited

U.S. PATENT DOCUMENTS

| | | | | |
|---|---|---|---|---|
| 6,076,908 A | * | 6/2000 | Maffeo | A47B 88/427 |
| | | | | 248/222.51 |
| 2005/0051723 A1 | | 3/2005 | Neagle | |

FOREIGN PATENT DOCUMENTS

| | | |
|---|---|---|
| DE | 10 2005 028 674 A1 | 12/2006 |
| DE | 102005028674 A1 | 12/2006 |
| DE | 10 2010 029 768 A1 | 12/2011 |
| DE | 102010029768 A1 | 12/2011 |
| EP | 2 042 811 A1 | 9/2007 |
| EP | 2 246 632 A1 | 11/2010 |
| FR | 2849862 | 7/2004 |
| WO | 8001449 A1 | 7/1980 |
| WO | 2011130865 A2 | 10/2011 |

OTHER PUBLICATIONS

International Bureau of WIPO, PCT International Report on Patentability, English Translation, dated Oct. 7, 2016, p. 1-18, International Application No. PCT/EP2015/055587, Applicant: Andreas Hettich GMBH.
International Bureau of WIPO, PCT International Report on Patentability, dated Sep. 29, 2016, p. 1-12, International Application No. PCT/EP2015/055587, Applicant: Andreas Hettich GMBH.

* cited by examiner

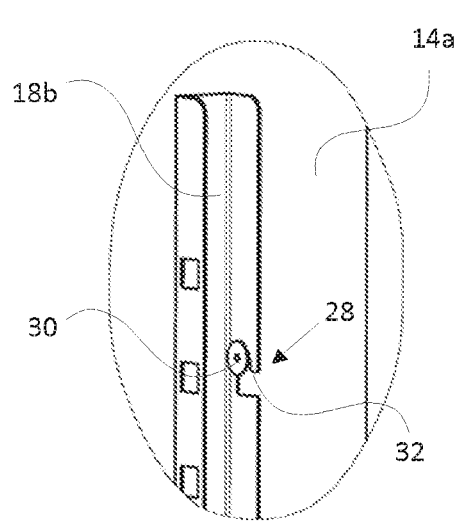
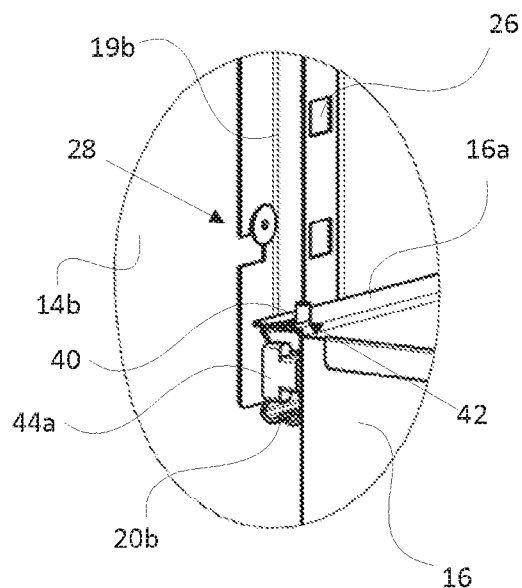
Fig. 5  Fig. 6
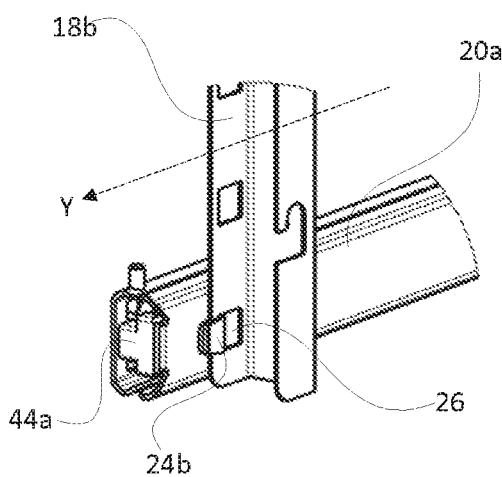
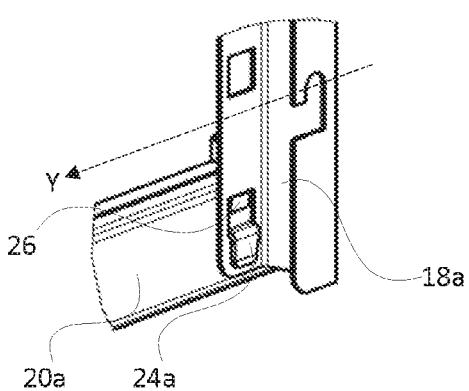
Fig. 7a  Fig. 7b

INCUBATOR

This patent application is the national phase entry of PCT/EP2015/055587. PCT/EP2015/055587, international application filing date Mar. 17, 2015, claims the benefit and priority of and to German patent application no. DE No. 10 2014 103 930.0, filed Mar. 21, 2014. PCT/EP2015/055587, international application filing date Mar. 17, 2015 and German patent application no. DE No. 10 2014 103 948.3, filed Mar. 21, 2014 are incorporated herein by reference hereto in their entireties.

The invention relates to an incubator.

A multitude of generic incubators are known which include a system for storing microorganisms to be incubated, said system being for the most part firmly embedded in the interior of the incubator. The incubators have interiors of the deep-drawn type, for example, in which one or plural trays are arranged at a fixed vertical position each and can be inserted or removed. Consequently, this design affords no flexibility regarding the amount of material to be incubated and/or the height of the containers holding the material since the spacing of the storage levels is fixed.

Furthermore, incubators with detachable drawers have also been proposed. This affords more flexibility with regard to the number and/or the height of the containers, because the spacing of the supports for the drawers can thus be varied more appropriately. However, this design makes cleaning considerably more difficult as there are a lot of problem locations—corners and recesses of the slide-in and support fixtures and spaces between them—which can only be cleaned with a lot of effort or not at all. Depending on each approach, the fixtures for inserting and supporting the drawers are either permanently attached to the drawer or to the interior space of the incubator, or connected to them in way that makes them very difficult to detach. Moreover, conventional guides often do not run smoothly and tend to jam.

It is the object of the invention to provide an incubator in accordance with the features stated in the preamble whose system of support and slide-in fixtures can be cleaned easily and whose drawers can be inserted and removed easily as well as arranged flexibly.

The invention is based on the finding that support and slide-in fixtures can be provided which can easily be detached both from the drawers and from the incubator itself. By making the surfaces to be cleaned large and flat, cleaning of the incubator, the drawers as well as the support and slide-in fixtures can thus be facilitated in a simple manner.

According to the invention, the incubator comprises a tray opening for inserting trays into an internal space which is bounded by walls, as well as telescopic rails having a first rail part which can be connected to a side wall and at least one further second rail part which can be connected to the tray. It is considered advantageous to form the telescopic rails as components separately from the internal space of the incubator and from the trays, to provide supports for the telescopic rails on the side walls, and to arrange for the trays to be detachable from the telescopic rails and for the telescopic rails to be detachable from the supports. As a result, those elements of the internal space of the incubator which are the most difficult to clean owing to their size and shape, i.e. the telescopic rails, can be easily removed and cleaned in a separate process specifically intended for this purpose. Moreover, this considerably increases the amount of flat surfaces in the internal space and in the tray, which also facilitates their cleaning.

To facilitate the cleaning process even more, the telescopic rails can be autoclaved. Time-consuming manual cleaning of the telescopic rails can thus be replaced with more effective automatic cleaning in an autoclave which definitely guarantees complete sterility.

In yet another advantageous embodiment of the invention, the supports are arranged on the side walls spaced at regular vertical intervals from each other, in particular in a line. Each side wall comprises at least two supports for each telescopic rail, said supports being preferably arranged in a horizontal plane. As a result, the trays are stably supported on at least four support points. Moreover, the vertical spacing of the trays may be chosen flexibly, depending on the height of the containers to be stored in them.

According to one aspect of the invention, the support is formed by a recess in the side wall and a latching element of the telescopic rail which engages the recess in the side wall, or vice versa. Such a latching connection can be obtained in a single movement and does not require any additional components, which in turn facilitates cleaning.

It is considered advantageous to form the support from one recess of a plurality of recesses in a vertical rail and a latching element of the telescopic rail which engages the recess in the vertical rail, or vice versa, and to provide at least two vertically spaced supports for the vertical rail, said supports for the vertical rail each being formed by a recess in the side wall and a latching element of the vertical rail which engages the recess in the side wall, or vice versa. This makes cleaning of the incubator even easier, at the same time retaining its easy height adjustment characteristic, since this first of all clearly reduces the number of recesses and/or latching elements in the side wall, and secondly, the vertical rails can be easily detached from the side wall and cleaned separately, in particular in an autoclave if they are of an autoclavable design.

It is particularly favourable if the trays can be detached from the telescopic rails, and the telescopic rails can be detached from the supports, without the use of tools. This allows quick removal of the parts contained in the internal space of the incubator, which notably makes the separate process of cleaning the telescopic rails clearly more efficient.

When the support is formed by a bayonet catch, the trays will be supported in a particular stable and reliable manner.

It is favourable to provide the telescopic rails with stop means so as to limit the amount of travel of the tray on the telescopic rail in the internal space. For this purpose, a stop each is provided on the first rail part and on the second or third rail parts, which stops are positioned such that the rail parts can only be slid relative to each other up to a certain pre-determined position in the slide-in direction. At this position, the two stops will make contact with each other, and the stop provided on the first rail part will then block further travel of the stop provided on the second or third rail parts. This makes it easier to lock the tray in position.

In an advantageous further development of the invention, the stop means is provided with a stop pad for cushioning the stop of the tray when the latter is fully inserted. The stop pad may be a flexible element, made of rubber or plastic for example, which is affixed to, in particular fitted on, the stop provided on the first rail part, and can be easily removed for cleaning and in particular for autoclaving. This reduces the risk of the material to be incubated slipping out of its original position in the tray or even being spilt when too much force is applied for inserting the tray into the incubator.

With a view to achieving a particular long service life of the telescopic rails, stainless steel is preferably used for their manufacture. Stainless steel is scratch-proof and abrasion-resistant as well as resistant to acids and bases. Moreover, it can be autoclaved and is thus rust-proof and temperature-resistant. Even after rough treatment over a prolonged period of time, stainless steel will thus not provide a surface for the adherence of germs.

According to a further aspect of the invention, for fixing the tray in the direction of the longitudinal axis of the telescopic rail, latching devices are provided to connect the telescopic rail to the tray. These latching devices have latching means such as hooks or pins on one side thereof and associated recesses on their other side. Consequently, a single movement during insertion of the tray will suffice to achieve a latching connection between the telescopic rails and the trays, without requiring any additional components—which in turn facilitates cleaning.

It is advantageous to have a set of trays of different heights, with the heights of the trays and the heights of the supports being matched to one another. Use of the incubator storage space can thus be optimized when storing containers of different heights or vertically stacked containers in the trays.

Additional advantages, features and possible applications of the present invention may be gathered from the description which follows, in which reference is made to the embodiments illustrated in the drawings.

Throughout the description, the claims and the drawings, those terms and associated reference signs are used as are listed in the List of Reference Signs which follows below. In the drawings, FIG. 1 is a perspective view of the incubator;

Figure 2:
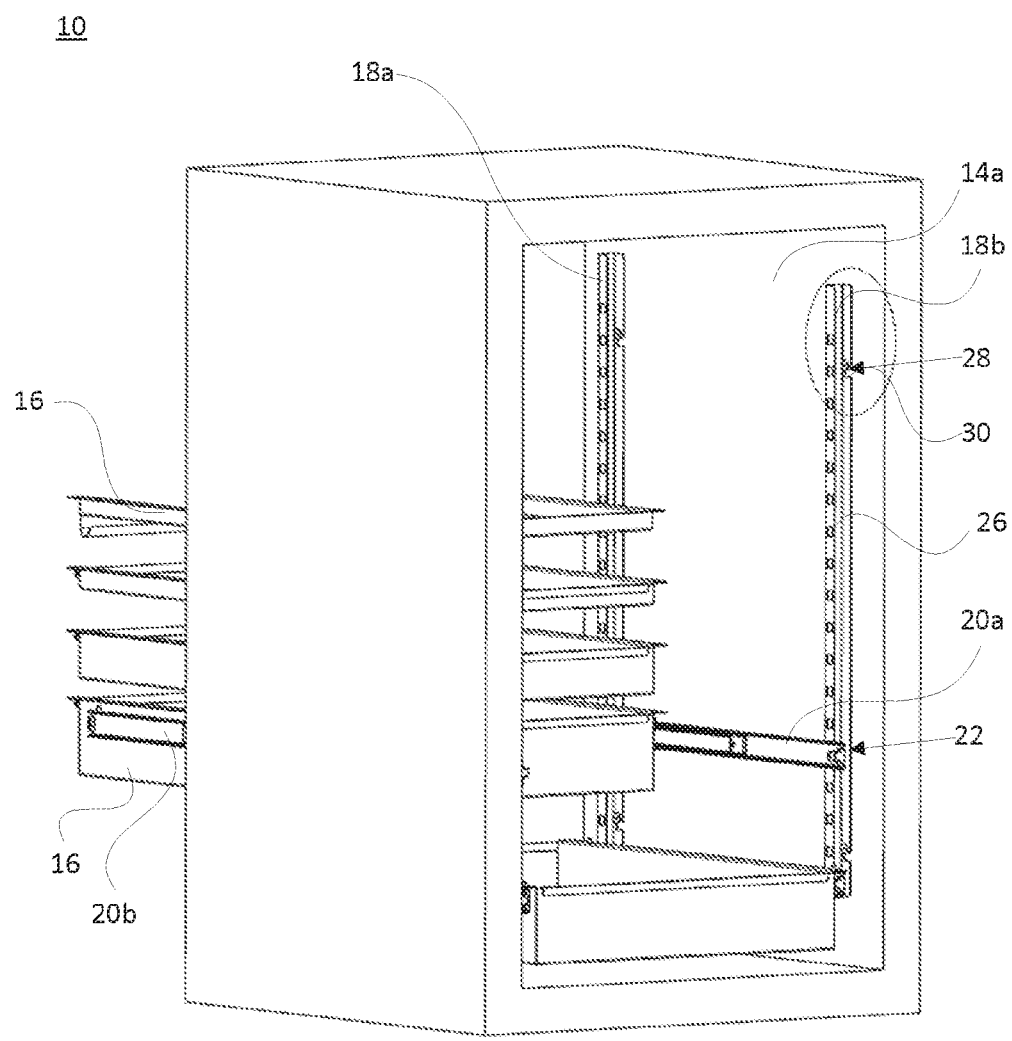
FIG. 2 is a perspective rear view of the incubator.
Figure 3:
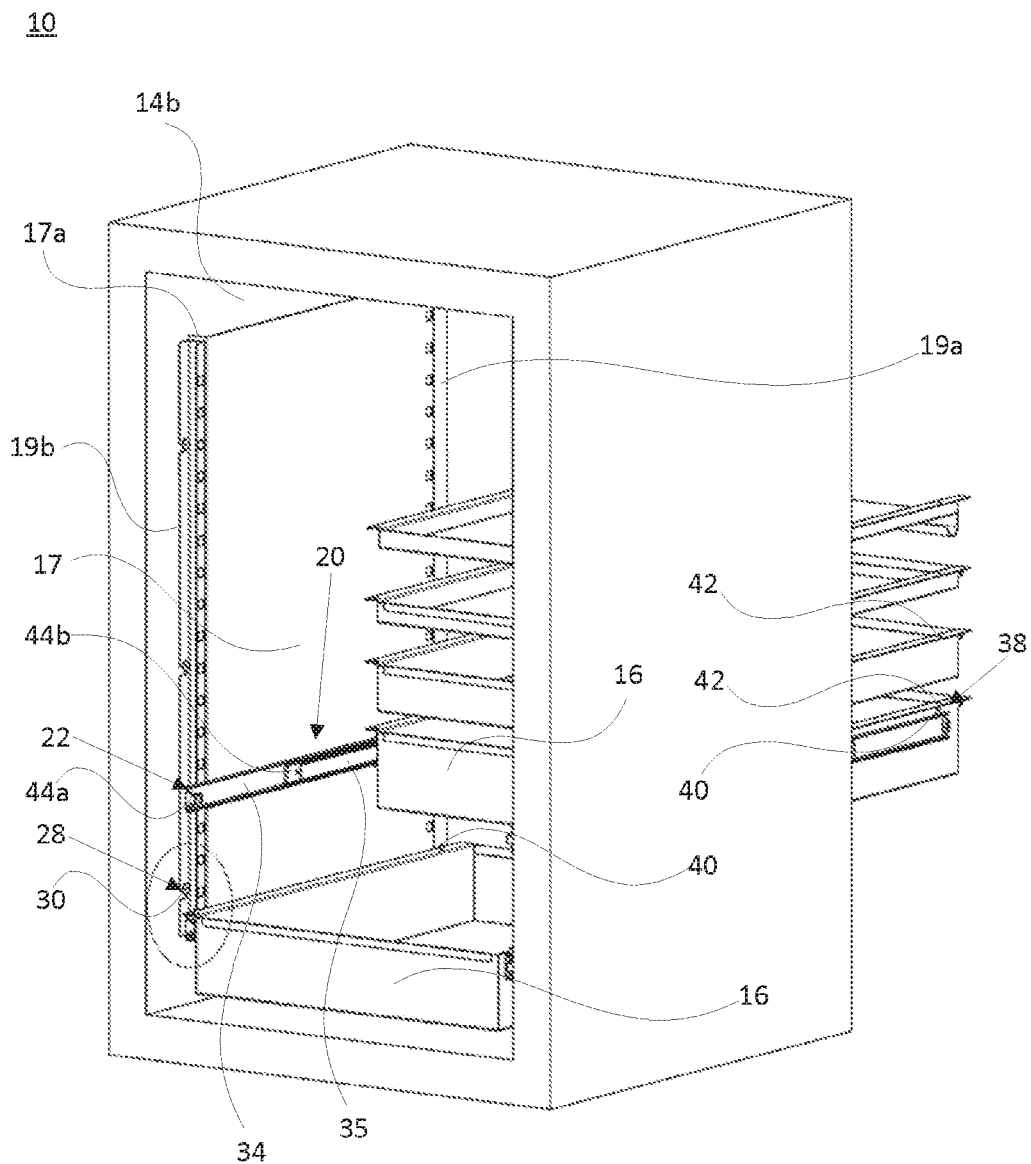
FIG. 3 is another perspective rear view of the incubator, in which the rear wall of the incubator has been omitted for reasons of clarity.
Figures 4A, 4B:
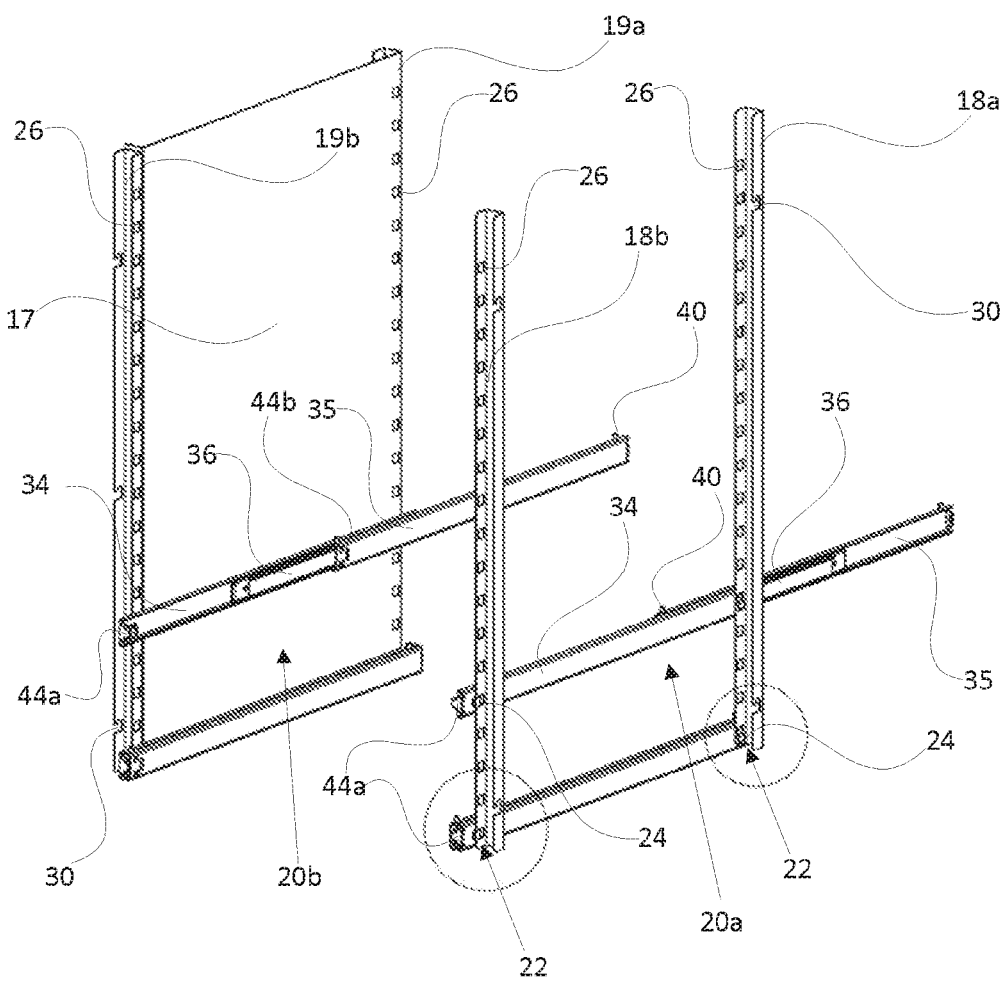

FIG. 4a a partial view of the telescopic rails and the vertical rails with connection plate;

FIG. 4b a partial view of the telescopic rails and the vertical rails;

FIG. 5 an enlarged view of a detail of FIG. 2;

FIG. 6 an enlarged view of a detail of FIG. 3;

FIG. 7a an enlarged view of a detail of FIG. 4, and

FIG. 7b an enlarged view of a detail of FIG. 4.

Figure 1:
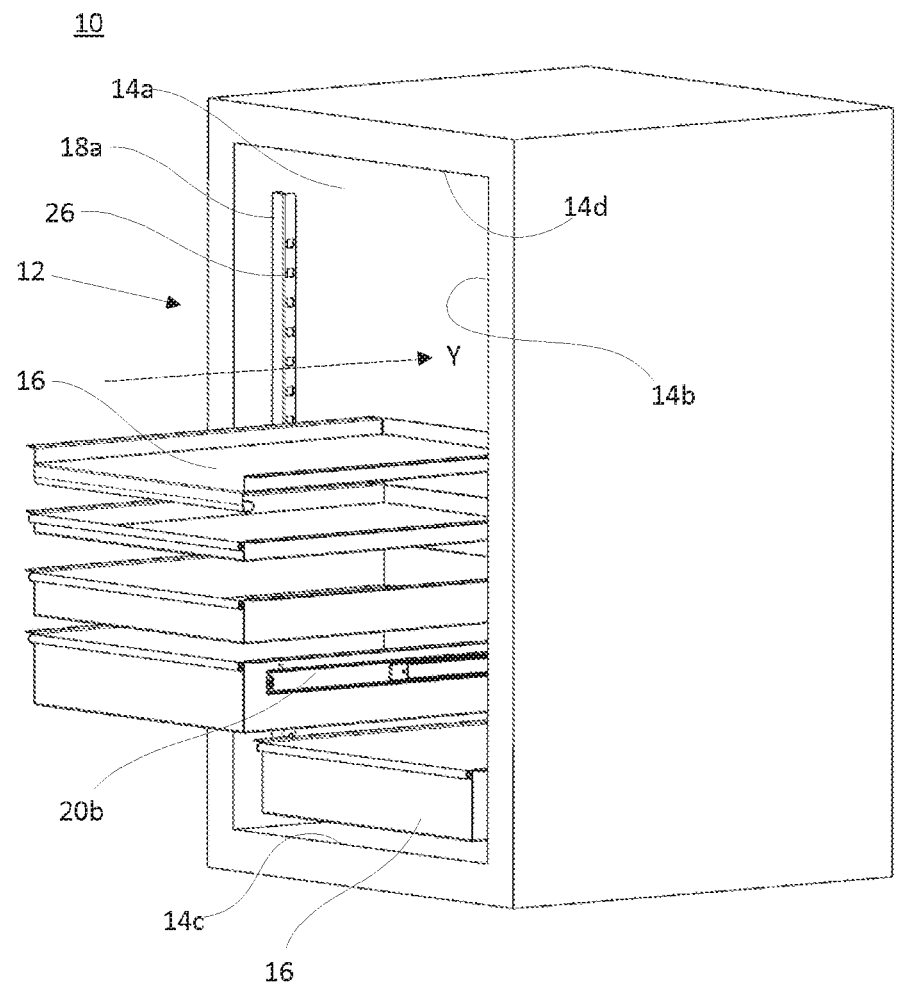

FIG. 1 is a perspective view of an incubator 10 according to the invention. Protruding from a tray opening 12 are four trays 16 which have been pulled out to some extent, a fifth tray 16 is completely inserted in the incubator 10. The trays 16 are different in height.

Mounted on the left side wall 14a and on the right side wall 14b each are two vertical rails 18a, 18b. However, only the vertical rail 18a of side wall 14a which is closer to the tray opening 12 can be viewed in FIG. 1. The vertical rails 18a, 18b have a plurality of recesses 26 which are disposed vertically on top of one another. The arrangement and function of the vertical rails 18a, 18b are illustrated in more detail in FIGS. 2 to 4. The internal space of the incubator 10 is bounded by the side walls 14a and 14b, the base 14c, the top 14d and a rear wall which has been omitted from this view for reasons of clarity. The tray opening 12 is closed in a conventional manner by a door (not shown). In order to create predetermined climatic conditions in the incubator 10, suitable aggregates are provided. As these are of a conventional design, they are not described in more detail here.

The upper edges of both sides of the trays 16, which extend in parallel to the insertion direction Y, are provided with guide rails 16a via which the trays are supported on telescopic rails 20a and 20b provided on both sides between the trays 16 and the side walls 14a, 14b. For reasons of clarity, this perspective view only shows one telescopic rail 20b, on the second tray 16 from the bottom. The telescopic rails 20 will be described in more detail below with reference to FIGS. 4 to 7.

FIG. 2 is a perspective rear view of the incubator 10 without its rear wall. This drawing shows the two vertical rails 18a, 18b mounted on the side wall 14a, as well as the two telescopic rails 20a and 20b which are each supported on vertical rails 18a and 18b, said telescopic rails 20a and 20b in turn supporting the second tray 16 from the bottom. The vertical rails 18a, 18b have two further recesses 30—in addition to the recesses 26 each constituting part of the supports 22 for the telescopic rails 20a and 20b that are explained in more detail with reference to FIGS. 4 and 7a—which each form part of supports 28 explained in more detail with reference to FIGS. 5 and 6, said supports 28 connecting the vertical rails 18a, 18b to the side walls 14a, b. In order to provide good stability, the supports 28 are each located adjacent the upper and lower ends of the vertical rails 18a, 18b.

It is also possible to omit the vertical rails 18a, 18b and to design the supports such that the recesses are made in the side walls 14a, b which the latching elements 24 of the telescopic rails 20a, 20b will then engage.

FIG. 3 is another perspective rear view of the incubator 10 without its rear wall. This view shows an alternative solution in which two vertical rails 19a and 19b are permanently connected to one another by a connection plate 17. In order to balance the additional weight of the connection plate 17 and to achieve better stability, three supports 28 each are provided for connection between the vertical rails 19a, 19b and the side walls 14a, b, which supports 28 are located at the upper and lower ends and about half way up the length of the vertical rails 19a, 19b. The connection plate 17 is integrally formed with the vertical rail 19a. The rail 19b is connected to a connection wall 17a which is vertically aligned with the side wall 14b. The connection wall 17a in turn is integrally formed with the connection plate 17 and adapted to the dimensions of the rail 19b.

The telescopic rails 20 have two latching pins 40 each which will engage two assigned recesses 42 on the respective guide rail 16a of the tray 16 during insertion of the latter. More specifically, the latching pins 40 will vertically pass through the recesses 42. Together, these latching pins 40 and recesses 42 form latching devices 38. Their weight, as well as the action of these latching devices 38 ensure that the trays 16 are reliably supported on the telescopic rails 20 and can be inserted into and/or pulled out of the incubator 10 without the danger of slipping or falling down.

As can be seen more clearly in FIG. 4a, the telescopic rails 20 are composed of plural parts. Mounted on a first rail part 34 intended for the connection plate 17 is a first stop 44a, and mounted on a second rail part 35 intended for the tray 16 is a second stop 44b. The two stops 44a and 44b together form a stop means 44. In the process of inserting the tray 16, the second rail part 35 can only be slid relative to the first rail part 34 up to a certain point where the two stops 44a and 44b will then abut each other. This will then block any further travel of the second rail part 35 and thus of the associated tray 16.

FIG. 4a is a view of the abovementioned solution with two vertical rails 19a and 19b which are permanently connected to each other by a connection plate 17. The vertical rails 19a and 19b are designed as U-section rails. On the side facing the trays 16 not shown in FIG. 4a, they are provided with a plurality of recesses 26 which will be engaged by latching elements 24 provided on the telescopic rails 20b. Together, these recesses 26 and latching elements 24 form supports 22 for fixing the telescopic rails 20 on the vertical rails 19a and 19b. Similarly, the supports 22 could be designed such that the telescopic rails 20b have recesses and the allocated latching elements are provided on the vertical rails 19a and 19b.

On the side facing the side wall 14b, the vertical rails 19a and 19b include further recesses 30 which are engaged by latching elements 32 provided on the side wall 14b. As already described with reference to FIGS. 2 and 3, the vertical rails 19a and 19b, which are connected to each other by a connection plate 17, each have three recesses 30. Consequently, three latching elements 32 each (not shown in FIG. 4a) are provided on the side wall 14b for a vertical rail 19a and 19b. Together, these recesses 30 and latching elements 32 form supports 28 which are shown in more detail in FIGS. 5 and 6, for supporting the vertical rails 19a and 19b on the side wall 14b. Similarly, the supports 28 could be designed such that the side wall 14b has recesses and the allocated latching elements are provided on the vertical rails 19a and 19b.

The telescopic rails 20b comprise three rail parts to make it possible at least to pull out the trays 16 (not shown in FIG. 4 for reasons of clarity) almost completely. The first rail part 34 is allocated to the side wall 14b and has two latching elements 24 which are spaced from each other at a distance which corresponds to the distance between the recesses 26. For a reliable and easy connection, the telescopic rails 20b can thus be made to latch into engagement with the rails 19a and 19b. The second rail part 35 is allocated to the respective tray 16 and has the latching pins 40 described with reference to FIG. 3. On the end of the first rail part 34 which is allocated to the vertical rail 19b, a stop pad has been affixed to the stop 44a (not shown here) in order to cushion the impact of the stops 44a and 44b making contact when the second rail part 35 is moved. Various elastic materials can be chosen for producing the stop, in the present embodiment rubber is used. The stop pad can merely be fitted onto the stop and can be easily removed for facilitated cleaning.

In a known manner, the first rail part 34 and the second rail part 35 are permanently connected to each other via a third rail part 36.

FIG. 4b shows the above mentioned solution, in which the telescopic rails 20a are connected to two individual vertical rails 18a and 18b which are allocated to the side wall 14a. This solution merely differs from the solution illustrated in FIG. 4a, apart from missing the connection plate 17 and the connection wall 17a, in that the vertical rails 18a and 18b only have two recesses 30 each, instead of three recesses 30. Consequently, two latching elements 32 each are provided on the side wall 14a for a vertical rail 18a and 18b. As for the rest, the structure and arrangement of telescopic rails 20a and vertical rails 18a and 18b and their connection to each other and/or to the side wall 14a as well as the use of stop pads are the same as those described with reference to FIG. 4a.

FIG. 5 is an enlarged view of a detail marked in FIG. 2. The vertical rail 18b is supported in a support 28 which consists of a recess 32 provided in the rail 18b and a latching element 30 provided in the side wall 14.

FIG. 6 is an enlarged view of a detail marked in FIG. 3. The vertical rail 19b is supported in a support 28 which is similar to the one illustrated in FIG. 5. A telescopic rail 20b is supported in the bottom-most recess 26 of the vertical rail 19b. A tray 16 is in turn supported on the telescopic rail 20b, with a latching device 38 horizontally fixing the tray 16 in place. The latching device 38 comprises a latching pin 40 provided on the telescopic rail 20b and a recess 42 provided in a guide rail 16a of the tray 16, with the latching pin 40 passing vertically through the recess 42 as the tray 16 is inserted.

FIG. 7a is a view of a detail marked in FIG. 4. In this case, the telescopic rail 20a is supported in the bottom-most recess 26 of a vertical rail 18b. The latching element 24b is in the form of a clip pointing in the insertion direction Y.

FIG. 7b is a view of another detail marked in FIG. 4. In this case, the telescopic rail 20 is supported in the bottom-most recess 26 of the vertical rail 18a. The latching element 24a is formed as a clip which points downward perpendicular to the insertion direction Y.

The different orientation of the latching elements 24a and 24b, i.e. latching element 24a pointing in the insertion direction Y and latching element 24b pointing downward perpendicular to the insertion direction Y, serves to stabilize the telescopic rail 20 in these two directions.

In principle, in each of the latching connections discussed above, the positions of latching element and recess can also be reversed. The arrangements used here have been chosen with a view to making operation and cleaning of the incubator 10 of the invention as easy as possible.

LIST OF REFERENCE SIGNS 10 incubator
12 tray opening
14a left side wall
14b right side wall
14c base
14d top
16 trays
16a guide rail
17 connection plate
17a connection wall
18a,b vertical rails
19a, b vertical rails
20 telescopic rails
22 support
24 latching elements
26 recesses
28 support
30 further recesses
32 latching elements
34 first rail part
35 second rail part
36 third rail part
38 latching device
40 latching pin
42 recess
44 stop means
44a first stop
44b second stop

What is claimed is:

1. An incubator (10) for creating and maintaining a microclimate with controlled air humidity and temperature conditions, comprising:
    an internal space;
    said internal space is bounded by walls, a first sidewall (14a) and a second sidewall (14b), a wall (14c) is a bottom wall, and, a wall (14d) is a top wall;
    a tray (16), said tray includes at least two guide rails (16a), each of said at least two guide rails (16a) includes at least two recesses (42);
    a tray opening (12);

said tray opening (12) for inserting said tray (16) into said internal space bounded by said walls (14a, 14b, 14c, 14d);

each of said first sidewall (14a) and said second sidewall (14b) includes:

a first removable vertical rail (18a) removably attached to said first sidewall (14a) and a second removable vertical rail (18b) removably attached to said second side wall (14b);

said first removable vertical rail (18a) includes a recess (30) in said vertical rail (18a) and said second removable vertical rail (18b) includes a recess (30) in said vertical rail (18b);

at least two latching elements (32) mounted therein;

said first removable vertical rail (18a) includes a plurality of recesses (26) and said second removable vertical rail (18b) includes a plurality of recesses (26);

said at least two latching elements (32) removably engaging said recess (30) in said first removable vertical rail (18a) removably affixing said first removable vertical rail (18a) to said first sidewall (14a);

said at least two latching elements (32) removably engaging said recess (30) in said second removable vertical rail (18b) removably affixing said second removable vertical rail (18b) to said second sidewall (14b); and, a removable telescopic rail (20a, 20b), said removable telescopic rail (20a, 20b) includes a first rail part (34) and a second rail part (35), said first rail part 34 of said removable telescopic rail (20a, 20b) includes a first latch (24) removably engaging one of said plurality of recesses (26) of said first removable vertical rail 18(a) and a second latch (24) removably engaging one of said plurality of recesses (26) of said second removable vertical rail 18(b) and, said second rail part (35) includes at least two latching pins (40), and each of said at least two latching pins (40) removably engaging one of said recesses (42) of one of said guide rails (16a) of said tray (16); and, said guide rails (160) of said tray engaging said second part (35) of said telescopic rail.

2. The incubator as claimed in claim 1, further comprising:

said first and second telescopic rails (20a, 20b) are autoclaved when removed from said incubator.

3. The incubator as claimed in claim 1, further comprising: each of said telescopic rails (20a, 20b) is detachable from said vertical rails (180, 180) for cleaning without the use of tools; and, said tray is detachable without the use of tools.

4. The incubator as claimed in claim 1, further comprising: said latch (24) and said recess (26) removable engagement is a bayonet catch connection.

5. The incubator as claimed in claim 1, further comprising:

each of said telescopic rails (20a, 20b) includes a stop means (44) for limiting the amount of travel of said trays (16) of said telescopic rails (20) in said internal space.

6. The incubator as claimed in claim 5, further comprising:

said stop means (44) includes a stop pad for cushioning the impact of said tray (16) as it is being inserted into said incubator.

7. The incubator as claimed in claim 5, further comprising:

said telescopic rails (20a, 20b) are made of stainless steel.

8. The incubator as claimed in claim 5, further comprising:

a plurality of said trays (16);
said trays (16) have different heights.

* * * * *